United States Patent
Shim et al.

(10) Patent No.: US 8,198,658 B2
(45) Date of Patent: Jun. 12, 2012

(54) DEVICE AND METHOD FOR DETECTING BIOMOLECULES USING ADSORPTIVE MEDIUM AND FIELD EFFECT TRANSISTOR

(75) Inventors: Jeo Young Shim, Yongin-si (KR); Kyu Tae Yoo, Seongnam-si (KR); Won Seok Chung, Hwaseong-si (KR); Jung Im Han, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 271 days.

(21) Appl. No.: 12/125,506

(22) Filed: May 22, 2008

(65) Prior Publication Data
US 2008/0308846 A1    Dec. 18, 2008

(30) Foreign Application Priority Data

Jun. 13, 2007 (KR) .................. 10-2007-0057859
Aug. 20, 2007 (KR) .................. 10-2007-0083397

(51) Int. Cl.
*H01L 29/72* (2006.01)
(52) U.S. Cl. ............. 257/253; 257/48; 73/53.01; 435/4; 435/6
(58) Field of Classification Search .............. 257/48, 257/253; 73/53.01; 435/4, 6
See application file for complete search history.

(56) References Cited

U.S. PATENT DOCUMENTS

| | | | |
|---|---|---|---|
| 4,238,757 A | 12/1980 | Schenck | |
| 4,777,019 A | 10/1988 | Dandekar | |
| 4,960,722 A | 10/1990 | Ogawa | |
| 5,160,597 A | 11/1992 | Colapicchioni et al. | |
| 5,466,348 A | 11/1995 | Holm-Kennedy | |
| 6,210,977 B1 | 4/2001 | Sieben et al. | |
| 6,914,279 B2 | 7/2005 | Lu et al. | |
| 7,075,428 B1 | 7/2006 | Oleynik | |
| 2002/0006632 A1 | 1/2002 | Ponnampalam et al. | |
| 2002/0022203 A1* | 2/2002 | Habu et al. ................ | 430/620 |
| 2002/0117659 A1 | 8/2002 | Lieber et al. | |
| 2003/0073071 A1* | 4/2003 | Fritz et al. ................ | 435/4 |
| 2003/0102510 A1 | 6/2003 | Lim et al. | |
| 2004/0033627 A1 | 2/2004 | Aytur et al. | |
| 2004/0132070 A1 | 7/2004 | Star et al. | |
| 2004/0195563 A1 | 10/2004 | Bao et al. | |
| 2005/0040483 A1 | 2/2005 | Offenhauser et al. | |
| 2005/0079598 A1 | 4/2005 | Davis | |

(Continued)

FOREIGN PATENT DOCUMENTS

EP    1348951 A1    10/2003

(Continued)

OTHER PUBLICATIONS

Hodge-Miller, "Gateless Depletion Mode Field Effect Transistor for Macromolecule Sensing". 2003, pp. 918-921, IEEE.

(Continued)

*Primary Examiner* — Edward Wojciechowicz
(74) *Attorney, Agent, or Firm* — Cantor Colburn LLP

(57) ABSTRACT

A device for detecting biomolecules includes: a semiconductor substrate; a source region and a drain region separately provided at the substrate; a chamber formed at the substrate including a region between the source region and the drain region, the chamber configured to contain a sample including the biomolecules; and an electrode which applies a voltage to the sample in the chamber. The biomolecules are mobile with respect to the electrode and sample. Methods for detecting biomolecules are also disclosed.

15 Claims, 5 Drawing Sheets

U.S. PATENT DOCUMENTS

| | | |
|---|---|---|
| 2005/0170347 A1 | 8/2005 | Miyahara et al. |
| 2005/0230271 A1 | 10/2005 | Levon et al. |
| 2006/0011911 A1* | 1/2006 | Bockelmann et al. ......... 257/48 |
| 2006/0141474 A1* | 6/2006 | Miyahara et al. ................ 435/6 |
| 2006/0197118 A1 | 9/2006 | Migliorato et al. |
| 2006/0205013 A1 | 9/2006 | Shim et al. |
| 2007/0251301 A1* | 11/2007 | Lee et al. .................... 73/53.01 |
| 2009/0322354 A1 | 12/2009 | Yoo et al. |

FOREIGN PATENT DOCUMENTS

| | | |
|---|---|---|
| JP | 2003322633 | 11/2003 |
| JP | 2004004007 | 1/2004 |
| WO | 0201647 A1 | 1/2002 |
| WO | 2005121765 | 12/2005 |

OTHER PUBLICATIONS

Besselink et al. "Modification of ISFETs with a monolayer of latex beads for specific detection of proteins" Biosensors and Bioelectronics 18, 2003, pp. 1109-1114.

European Examination Report for application No. 08157178.8-1240 dated Oct. 10, 2011.

Yu et al. "A comparative study of PCR product detection and quantitation by electrochemiluminescence and fluorescence" Journal of Bioluminescence and Chemiluminescence, vol. 10, Issue 4, pp. 239-245, published online Mar. 30, 2005.

Ayers et al. "A Microfluidic Diagnostic Chip Integrating DNA Extraction, Amplification & Detection" Micro & Nano Technology (MNT) Measurement Club, Dec. 2005.

* cited by examiner mixture of PCR product

DEVICE AND METHOD FOR DETECTING BIOMOLECULES USING ADSORPTIVE MEDIUM AND FIELD EFFECT TRANSISTOR

The present invention claims priority to Korean Patent Application No. 10-2007-0057859, filed on Jun. 13, 2007, and Korean Patent Application No. 10-2007-0083397, filed on Aug. 20, 2007, and all the benefits accruing therefrom under 35 U.S.C. §119, the contents of which in their entirety are herein incorporated by reference.

BACKGROUND OF THE INVENTION

1. Field of the Invention

The present invention relates to a device and a method for detecting the existence or the concentration of biomolecules using a field effect transistor.

2. Description of the Prior Art

A transistor-based biosensor is a type of detection device containing transistors therein, which detects biomolecules with electric signals. The transistor-based biosensor is a sensor fabricated using a semiconductor process. It has advantages in that the conversion of the electric signals is fast, and the transistor-based biosensor is relatively easy to dispose on an integrated circuit ("IC") or a microelectromechanical system ("MEMS").

Among transistor-based biosensors, a field effect transistor ("FET") based biosensor is the representative device for measuring biological reactions. In the case of such an FET based biosensor, final products are usually compact detectors suitable for lab-on-a-chip devices or point-of-care products. Conventional FET-based biosensors measure surface charge density, commonly present within a Debye length, and measure electric signals from biomolecules adsorbed on the gate surface. Therefore, in order to use such FET-based biosensors, the biomolecules are essentially fixed to the gate surface of the FET.

BRIEF SUMMARY OF THE INVENTION

The present invention relates to a device and a method for detecting biomolecules using an adsorptive medium.

The device according to the invention comprises a source region and a drain region separately provided at a semiconductor substrate; a chamber provided at the semiconductor substrate including a region between the source region and the drain region, the chamber being configured to contain a sample including the biomolecules; and an electrode which applies a voltage to the sample in the chamber, wherein the biomolecules are mobile with respect to the electrode and sample.

The device according to an exemplary embodiment of the present invention includes an adsorptive medium having an adsorptive site on which the biomolecules can be adsorbed.

When a sample containing the biomolecules is introduced into the chamber of the device, and a voltage is applied to the electrode, a channel between the source region and the drain region is formed. Then, the biomolecules in the sample can be detected by measuring the quantity of current and/or voltage in the channel.

The device according to an exemplary embodiment of the present invention may comprise a means for measuring the electrical signal (e.g., current and/or voltage) generated in the channel by the voltage applied to the electrode.

In an exemplary embodiment, the electric signal measured in the device is a source-drain current or a source-drain voltage.

The device according to an exemplary embodiment of the present invention may further comprise a means for heating the sample in the chamber.

In an exemplary embodiment, the adsorptive medium is made of a material selected from a group including glass, silicone, plastic and magnetic substances. The adsorptive medium may be coated with a material chargeable for adsorption of the biomolecules, or a material capable of stacking interaction with the biomolecules. In an exemplary embodiment, the adsorptive medium takes the form of a bead.

The biomolecules to be detected are deoxyribonucleic acids ("DNAs"), ribonucleic acids ("RNAs"), proteins, carbohydrates, peptide-nucleic acids ("PNAs"), and their conjugates. In an exemplary embodiment of the present invention, DNA is detected using a glass adsorptive medium coated with polyethyleneimine.

The present invention also provides a method for detecting biomolecules using an adsorptive medium by means of a field effect transistor. The method includes the steps of: (a) reacting an adsorptive medium having, on a surface thereof, sites onto which the biomolecules can non-covalently adsorb biomolecules in a sample, thereby inducing the adsorption of the biomolecules to be detected; (b) positioning the adsorptive medium processed in step (a) between a source region and a drain region of the field effect transistor; and (c) measuring the electric signal between the source and drain regions. The field effect transistor is devoid of a gate electrode layer. In step (c), the adsorptive medium processed in step (a) may be introduced into a chamber positioned between the source region and the drain region of the FET.

In another aspect of the present invention, the method further includes the steps of, after performing steps (a) to (c), (d) reacting an adsorptive medium which was not reacted with the sample in step (a) with a buffer solution without the biomolecules; (e) positioning the adsorptive medium reacted with the buffer solution in step (d) between the source region and the drain region of the field effect transistor; (f) measuring an electric signal between the source and drain regions; and (g) comparing the electric signal measured in step (c) with the electric signal measured in step (f). In step (e), the adsorptive medium reacted with the buffer solution in step (d) may be introduced in a chamber positioned between the source region and the drain region of the FET. When employed, this method can determine the concentration of the biomolecules by comparing the result of the sample containing the biomolecules with that of a control sample (e.g., a buffer solution) devoid of the biomolecules.

In a still another aspect of the present invention, the method for detecting biomolecules (e.g., DNAs) includes the steps of: (a) introducing a sample containing the adsorptive medium on which the biomolecules are adsorbed into a chamber of the device for detecting biomolecules; (b) removing impurities by washing the sample in the chamber; (c) denaturing the biomolecules by heating the sample; and (d) detecting the biomolecules by measuring an electric signal between the source and drain regions.

In a still another aspect of the present invention, the method for detecting biomolecules using an FET (e.g., DNAs) includes the steps of: (a) washing a sample containing an adsorptive medium on which the biomolecules are adsorbed to remove impurities; (b) introducing the washed sample into a chamber of the device for detecting biomolecules; (c) denaturing the biomolecules by heating the sample; and (d) detecting the biomolecules by measuring an electric signal between the source and drain regions.

In a still another aspect of the present invention, the method for detecting biomolecules (e.g., DNAs) includes the steps of:

(a) introducing a sample containing the biomolecules into a chamber of the device for detecting biomolecules, and adsorbing the biomolecules on an adsorptive medium which is provided in the chamber; (b) washing the sample containing the adsorptive medium on which the biomolecules are adsorbed in the chamber to remove impurities; (c) denaturing the biomolecules by heating the sample; and (d) detecting the biomolecules by measuring an electric signal between the source and drain regions.

In a still another aspect of the present invention, the present invention provides a method for detecting biomolecules using the adsorptive medium, which is capable of preventing the drift of a detected signal, by means of a field effect transistor. The method for detecting biomolecules includes the steps of: (a) positioning an adsorptive medium having, on the surface thereof, sites onto which the biomolecules can non-covalently adsorb, between the source region and drain region of the field effect transistor; (b) flowing a buffer solution devoid of the biomolecules to the adsorptive medium positioned in step (a) for reaction; and (c) measuring an electric signal between the source and drain regions to correct signal drift. The field effect transistor has no gate electrode layer. In step (a), the adsorptive medium may be introduced in a chamber positioned between the source region and the drain region of the FET.

In an exemplary embodiment, the measurement of the electric signal in step (c) includes applying a voltage between either one of the source and drain regions and the substrate, and measuring a signal generated by the voltage.

BRIEF DESCRIPTION OF THE DRAWINGS

The above and other aspects, features and advantages of the present invention will be more apparent from the following detailed description taken in conjunction with the accompanying drawings, in which.

DETAILED DESCRIPTION OF THE INVENTION

The present invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the description, details of well-known features and techniques may be omitted to avoid unnecessarily obscuring the presented embodiments of the invention.

According to the present invention, an adsorption reaction of a biomolecule to be detected occurs on the surface of an adsorptive medium having sites (e.g., adsorptive sites) where the biomolecules, such as DNA, for example, but not limited thereto, are able to be adsorbed. A solution containing the adsorptive medium is then introduced into a chamber which is positioned between source region and drain region on a modified field effect transistor ("FET"). Then, a corresponding change in an electric signal of the FET is measured.

The present invention provides a method for detecting biomolecules by adsorbing the biomolecules on the adsorptive medium surface in a non-covalent bonding manner without immobilizing the biomolecules in a sample or a probe for detecting the biomolecules on the surface of a detection device. In the prior art, if the biomolecules or the detector is not immobilized on the gate surface of the FET, it is difficult to detect a biomolecule sample having a low concentration. In the present invention, adsorption sites in the medium are provided, so that biomolecules, such as DNA, can be effectively quantified even at low concentrations.

Figure 1:
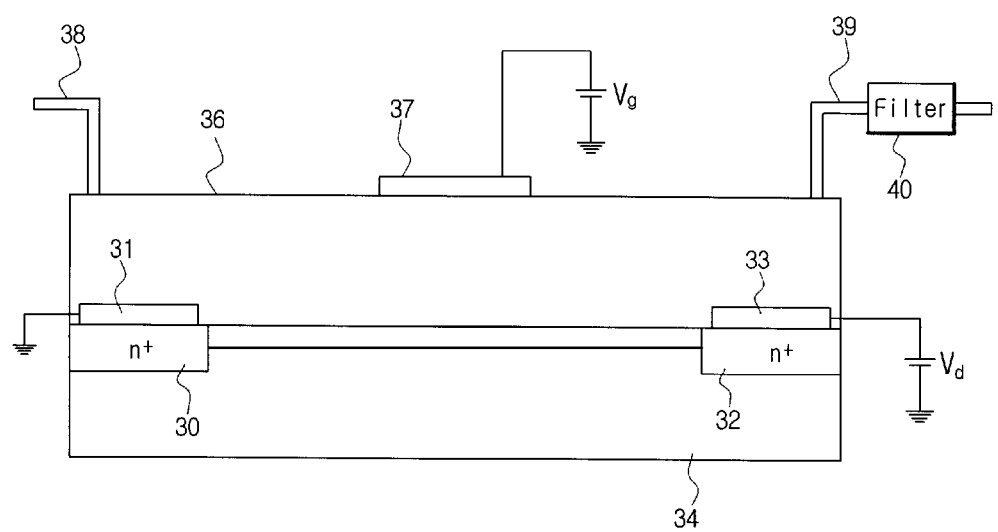
FIG. 1 is a schematic cross-sectional view of a biomolecule detection device according to an exemplary embodiment of the present invention.
Figure 2:
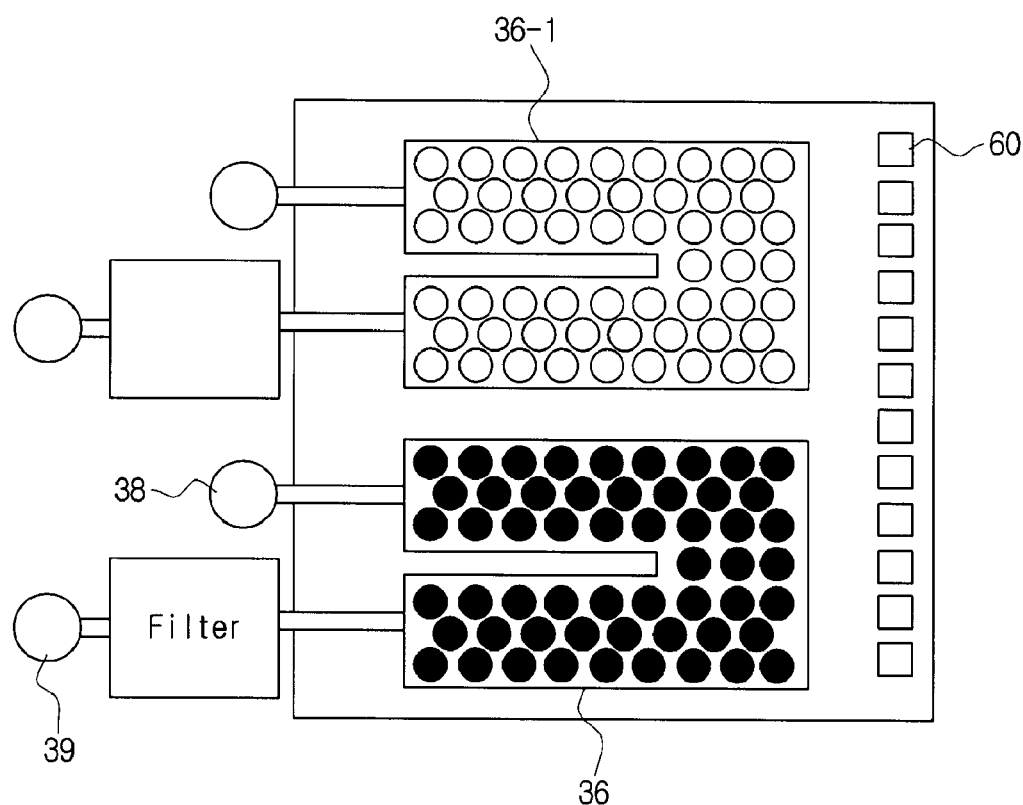
FIG. 2 is a plan view showing the biomolecule detection device of FIG. 1 according to an exemplary embodiment of the present invention.

FIG. 1 is a cross-sectional view and FIG. 2 is a plan view of a biomolecule detection device according to an exemplary embodiment of the present invention.

The detection device of the present invention uses the adsorptive medium between a source region and a drain region in a modified common FET as a generating device of an electric signal.

The transistor used in detection device shown in FIG. 1 is a modified FET fabricated by a complementary metal oxide semiconductor ("CMOS") process. The transistor has the construction including a p-type substrate (34) composed of a doped semiconductor material; a source region (30) and a drain region (32) separately formed on the substrate (34) and doped in a polarity opposite (indicated as "n+" in FIG. 1) to the substrate (34); and an electrode (37) ("reference electrode 37") applying a voltage to a sample contained in a chamber (36).

Such a modified FET has no gate electrode layer, which is generally included in a transistor. Instead of the gate electrode layer, the modified FET includes the electrode (37) corresponding to a gate electrode for applying a constant voltage thereto. When a voltage is applied to the electrode (37), a channel (35) (in FIG. 3D) is formed between the source region (30) and the drain region (32), and a current flows through the channel (35). By measuring the current flowing in the channel (35), the biomolecules in the sample may be detected and quantified.

As compared to the prior art common FET, the modified FET used in the exemplary embodiment of the detection device of the present invention is different in that a gate portion of the FET is modified. A suitable number of insulation layers may be provided on the substrate (34) of the present invention, which may be adjusted by those skilled in the art.

In the chamber (36), an inflow port (38) for flowing the sample into the chamber (36) and an outflow port (39) for flowing out the sample out from the chamber (36) may be provided. Further, a filter (40), for example, a partition, may be provided in the outflow port (39) for preventing the adsorptive medium, which is in the shape of bead, in the sample from flowing out of the chamber (36) when the sample is introduced into the chamber. Further, electrodes (31, 33) may be provided in the source region (30) and the drain region (32), respectively, to apply voltages. These electrodes (31, 33) are electrically connected to an electrode pad (60) (in FIG. 2) for applying external voltages to the electrodes (31, 33).

The biomolecule to be detected includes all biomolecules which can be adsorbed to the adsorptive medium with a proper adsorption force. A non-limited list of biomolecules may include deoxyribonucleic acids ("DNA"), ribonucleic acids ("RNA"), protein, carbohydrate, peptide-nucleic acid ("PNA"), conjugates of these molecules-glycoprotein, lipoprotein, protein-DNA complex, for example, but is not limited to the foregoing.

Since biomolecules such as proteins, nucleic acids, and carbohydrate carry many chargeable sites on their surfaces, they can interact with inorganic ions. An aqueous solution containing such charged biomolecules and counterions thereof has high concentrations of electrolytes, so that an ionic strength of the aqueous solution becomes higher. Nucleic acids can be stabilized by π-π interaction between adjacent nitrogen bases, and are characterized in that their bases "stack". That is, the planes of the nitrogen bases tend to pile on top of one another (e.g., stacking interaction). Since the π-π interaction, the essence of the stacking interaction, is a characteristic which aromatic flat rings generally share, it is known that aromatic side chains such as phenylalanine and tryptophan can also achieve the stacking interaction. Biomolecules such as DNA or protein can adsorb onto the surface of the adsorptive medium through stacking interaction with aromatic compounds (e.g., aromatic molecules such as ethidium bromide, indole, pyrene, or the like) or by electrostatic interaction with the opposite charge.

Upon being charged, biomolecules such as DNA or protein are accompanied by many counterions because of their large sizes. These counterions exert great influence upon the ionic strength of the aqueous solution containing the biomolecules. The characteristics of the induced channel current of the modified FET upon application of the voltage or the source-drain voltage in the case where the adsorptive medium with adsorbed biomolecules is positioned between the source region (30) and drain region (32) as described above differ greatly from those where a buffer solution containing simple inorganic salts is positioned in the same place, since the aqueous solution of the adsorptive medium with adsorbed biomolecules alters the ionic strength quite dramatically. Thus, the characteristics of electric signals from the modified FET vary depending on whether biomolecules exist in the aqueous solution.

In actual measurements, electrical signals from the modified FET for a solution containing an adsorptive medium treated with a sample ("sensing medium") are measured and compared with those detected for a solution containing the same adsorptive medium, but with no sample treatment ("reference medium") after applying a constant voltage by means of the reference electrode (37).

Since the detection of electrical signals by the device of the present invention is based on reversible interactions (electrostatic attraction, stacking interaction, and the like) between the biomolecules to be detected and the adsorptive medium, immobilization of these biomolecules on the substrate surface is not required. Therefore, exemplary embodiments of the present invention do not suffer from the inconvenience of immobilizing samples in advance. Especially, biomolecules can be cumulatively adsorbed onto the adsorption sites of the adsorptive medium if a dilute sample is repeatedly applied thereto. Thus, the present invention has an advantage in that it provides a method of detecting biomolecules in which dilute samples are concentrated.

For the sake of convenience, the device shown in FIG. 2 according to an exemplary embodiment of the present invention provides two separate chambers: one chamber (36-1) ("reference chamber") which is filled with reference beads and electrical signals are measured, and the other chamber (36) ("sensing chamber") which is filled with sensing beads and electric signals are measured. However, measurements using the exemplary embodiment of the present invention depicted in FIG. 2 do not necessarily require a separate FET device for each chamber (36, 36-1). According to the exemplary embodiment of FIG. 2, a detection device based on a single FET can alternate between the reference chamber (36-1) and the sensing chamber (36) with washing. In the device shown in FIG. 2, the reference medium (blank circle) without addition of sample and the sensing medium (filled circle) with addition of sample are filled in different chambers (36-1 and 36), respectively.

The sensing medium and the reference medium are positioned in the respective chamber between the source region (30) and the drain region (32) in a suspended state in solution. The suspension containing the adsorptive medium is introduced to the chamber, and then, a voltage is applied to the electrode (37), which corresponds to applying the voltage to a gate electrode in a common FET device. A current or a voltage measured between the source and the drain are examples of a detectable electric signal.

In the FET device of exemplary embodiments of the present invention, chambers are divided into the reference chamber (36-1) and the sensing chamber (36), distinguishable from each other either through spatial or temporal separation. The reference chamber (36-1) is filled with a adsorptive medium without adsorbed biomolecules, or a surface-treated adsorptive medium. In the case that the reference chamber (36-1) is filled with a surface-treated adsorptive medium, an electric signal can be detected by running a buffer solution without biomolecules. The drift of electrical signals can be corrected likewise.

Any material that affords surface treatment for adsorbing biomolecules or originally carries adsorption sites on its surface is suitable for the adsorptive media of the present invention. In exemplary embodiments, the adsorptive medium may be glass, silicone, plastic such as polyethylene, or magnetic material. The adsorptive medium may have a shape and a size suitable for adsorbing the target biomolecules. In one particular embodiment, the adsorptive medium may be a bead.

In exemplary embodiments of the present invention, surface treatments for the adsorptive medium includes coating the surface of these media with a material (e.g., adsorptive sites) capable of inducing the adsorption of target biomolecules through such interactions as electrostatic attraction or stacking interaction. Monomers and polymers with amino ("—$NH_2$") or imine ("—NH") groups are examples of a positively charged coating material. A monomer or polymer having carboxyl group (COOH) are examples of a negatively charged coating material. The material for stacking interaction may be an aromatic molecule including ethidium bromide, pyrene, or the like. In a particular exemplary embodiment of the invention, DNA to be detected is adsorbed onto a glass bead coated with positively charged polyethyleneimine or streptavidin.

Hereinafter, a method for detecting biomolecules according to an exemplary embodiment of the present invention will be described. FIGS. 3A to 3D are conceptual views of a biomolecule or an adsorptive medium in respective steps in the method for detecting biomolecules according to an exemplary embodiment of the present invention.

Figure 3A:
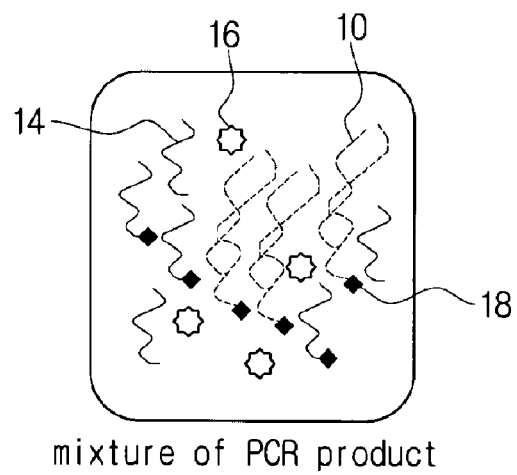
FIGS. 3A to 3D are conceptual views of a biomolecule or adsorptive medium in each respective step in a method for detecting biomolecules according to an exemplary embodiment of the invention.
Figure 3A:
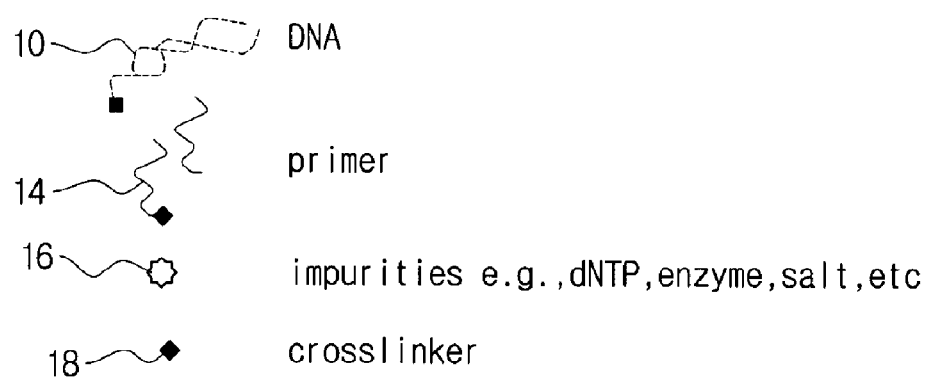

First, DNA is amplified using pressure cycling technology ("PCT"), for example, but is not limited thereto. In this case, the sample may comprise DNA (10), primer (14) used in the stage of polymerase chain reaction ("PCR") amplification, and impurities, such ANS-dNTP, enzyme, and salts as shown in FIG. 3A.

The primer (14) may be labeled by a material such as biotin, amine, epoxy, carboxyl acid, or thiol, for example, but not limited thereto, at an end terminal. Such material may form a crosslink with the adsorptive medium such as a bead in order to be adsorbed thereon. Therefore, such labeling material attached to the end terminal of the primer is referred as "crosslinker" (18) herein.

Figure 3B:
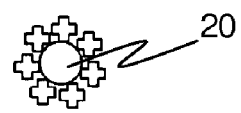
Figure 3C:
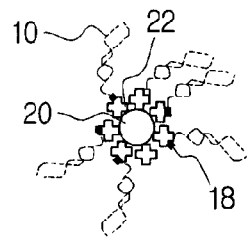

Then, the PCR products are mixed with the adsorptive medium (20) as shown in FIG. 3B so that DNA (10) among the PCR products may be adsorbed on the adsorptive medium (20) as shown in FIG. 3C.

Then, the sample containing the adsorptive bead, adsorptive medium (20) on which DNA (10) is adsorbed, is introduced into the chamber (36) of the device for detecting biomolecules.

Figure 3D:
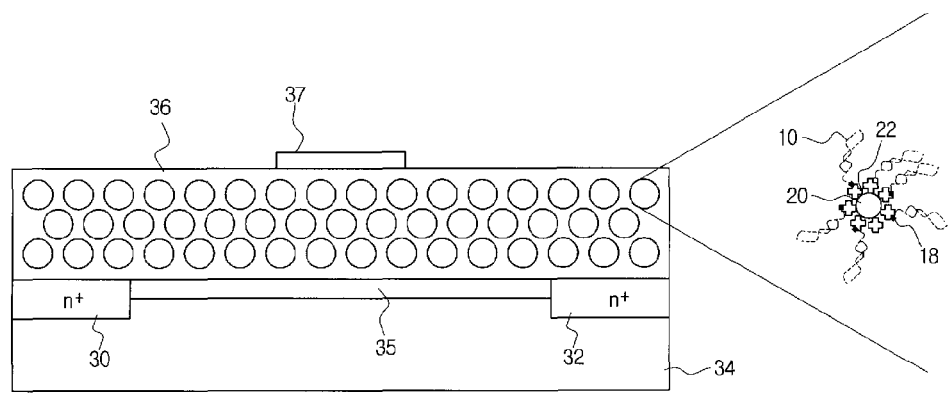

Then, a voltage is applied to the electrode (37) as shown in FIG. 3D so that the voltage is applied to the sample containing the adsorptive bead (20) on which DNA (10) is adsorbed. At this time, due to the ion strength of the sample, a channel (35) is formed between the source region (30) and the drain region (32). By measuring the current through the channel (35), DNA (10) in the sample is detected and the quantity of DNA (10) is measured.

Furthermore, exemplary embodiments of the present invention advantageously provide a detection device which can be reused by simple washing with a buffer solution. The adsorption of biomolecules in exemplary embodiments of the present invention takes place under low concentrations of inorganic salts so that the adsorption of biomolecules is strong enough to be sufficiently resistant to washing with buffer solutions whose conditions are close to those for physiological activity. However, the adsorbed biomolecules can be readily released by washing with buffer solutions with concentrated salts. Therefore, since the dissociation of adsorbed biomolecules can be achieved by simply changing the composition of the wash solution, the present invention is convenient to use.

Especially, a measurement error due to impurities (e.g., dNTP, enzyme, and salts, etc.) may be prevented by washing the sample contained in the chamber (36) with a buffer solution in order to remove the impurities other than the bead (20) on which DNA (10) is adsorbed.

Figure 4A:
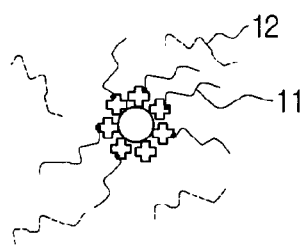
FIGS. 4A and 4B are conceptual views of a biomolecule or adsorptive medium in each respective step in a method for detecting biomolecules according to another exemplary embodiment of the invention.

After removal of the impurities, the sample is heated to about 90° C. Then, the DNA (10) in the sample is denatured, and the double stranded structure of the DNA (10) becomes a single stranded structure as shown in FIG. 4A.

Therefore, a single strand (11) of DNA adsorbed on the bead (20) remains on the bead, but the other single strand (12) of DNA which is a complementary strand of the adsorbed single strand (11) and moves freely in the space (e.g., gap) between the beads (20) in the sample.

Figure 4B:
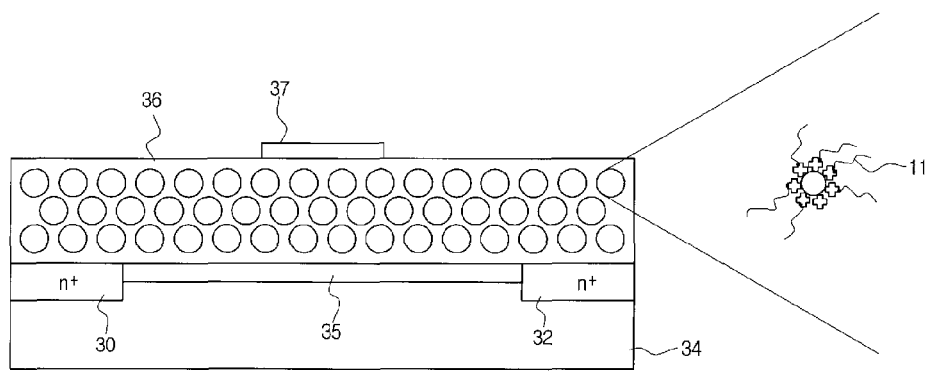

Then, in the state in which the sample is heated, and in which the DNA is denatured as mentioned above, a voltage is applied to the electrode (37) as shown in FIG. 4B. The voltage is applied to the sample containing the bead (20) on which the single strand (11) of DNA is adsorbed.

At this time, due to the ion strength of the single strand (11) of DNA which moves freely in the sample, a channel (35) is formed between the source region (30) and the drain region (32), and the current through the channel (35) is increased. By measuring the current through the channel (35), DNA (10) in the sample is detected and the quantity of DNA (10) is measured.

Figure 5:
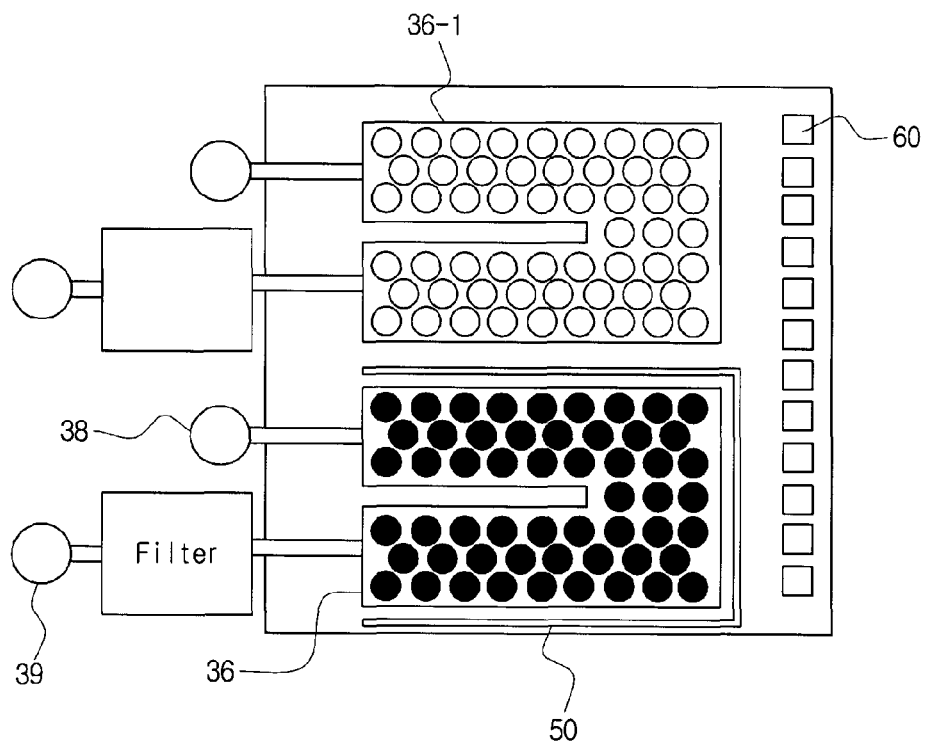
FIG. 5 is a plan view showing another biomolecule detection device according to an alternative exemplary embodiment of the present invention.

FIG. 5 is a plan view showing another biomolecule detection device according to an alternative exemplary embodiment. The device according to the present exemplary embodiment of the present invention illustrated in FIG. 5 includes a means (50) for heating in order to facilitate heating the sample in the chamber (36).

The means (50) for heating may be installed around or below the chamber (36). An electric resistor whose temperature is increased when it is connected to a power supply may be used as the means (50) for heating, for example, but is not limited thereto. When the means (50) for heating is connected to the power supply, heat is generated, and the heat is transferred to the chamber (36) through the substrate (34).

In the above described exemplary embodiments for a method of detecting biomolecules and a device for detecting biomolecules, the bead (20) on which PCR amplified DNA (10) was adsorbed is introduced into the chamber (36), and then, the sample in the chamber (36) is washed to remove the impurities. Alternatively, an exemplary embodiment of a method of detecting biomolecules or a device for detecting biomolecules may be configured such that the bead (20) on which DNA (10) was adsorbed is washed to remove impurities, and then the washed bead (20) on which DNA is adsorbed is introduced into the chamber (36).

Further, in the above described exemplary embodiments for a method of detecting biomolecules and a device for detecting biomolecules, the bead (20) is adsorbed with PCR amplified DNA (10), and then, the bead (20) on which DNA was adsorbed is introduced into the chamber (36). Alternatively, an exemplary embodiment of a method of detecting biomolecules or a device for detecting biomolecules may be configured such that the bead (20) was packed in the chamber (36) of the device, and DNA products are introduced into the chamber (36) so that the DNA (10) may be adsorbed on the bead (20) in the chamber (36), and then, the sample in the chamber (36) is washed to remove impurities.

The above described exemplary embodiments of a device and method for detecting biomolecules based on a field effect transistor ("FET") include using an adsorptive medium capable of non-covalently absorbing the biomolecules. This detection device has a detection limit lower than those of existing FET-based devices. In addition, this device does not require surface immobilization or pre-treatment of the biomolecules to be detected. Since this device produces dose-dependent signals, quantification of the biomolecules to be detected can be achieved as well.

The terminology used herein is for the purpose of describing particular embodiments only and is not intended to be limiting of the invention. The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

While the present invention has been described with reference to the particular exemplary embodiments and the accompanying drawings, it is not to be limited thereto but will be defined by the appended claims.

It is to be appreciated that those skilled in the art can substitute, change or modify the embodiments into various forms without departing from the scope and spirit of the present invention.

What is claimed is:

1. A device for detecting biomolecules comprising:
   a semiconductor substrate;
   a source region and a drain region separately provided at the substrate;
   a chamber formed at the substrate including a region between the source region and the drain region, the chamber configured to contain a sample including the biomolecules and an adsorptive medium on which the biomolecules can be adsorbed; and
   an electrode which applies a voltage to the sample in the chamber,
   wherein the biomolecules being detected are mobile with respect to the region between the source region and the drain region.

2. The device according to claim 1, wherein a channel is formed in the region between the source region and the drain region when the voltage is applied to the electrode, and the biomolecules in the sample are detected by measuring an electric signal through the channel.

3. The device according to claim 2, wherein the electric signal is at least one of a current through the channel and a voltage between the source region and the drain region.

4. The device according to claim 1, wherein the chamber is formed on the substrate including the source region and the drain region.

5. The device according to claim 1, wherein the adsorptive medium non-covalently absorbs the biomolecules.

6. The device according to claim 1, wherein the adsorptive medium is made of glass, silicone, plastic or magnetic material.

7. The device according to claim 1, wherein the adsorptive medium has a bead shape.

8. The device according to claim 1, wherein the adsorptive medium comprises adsorption sites on which the biomolecules can be adsorbed.

9. The device according to claim 8, wherein the adsorptive sites are made of one of a chargeable material and a material capable of stacking interaction with the biomolecules.

10. The device according to claim 8, wherein the adsorptive site is made of one of polyethyleneimine or streptavidin.

11. The device according to claim 1, further comprising a means for heating the sample in the chamber in thermal communication with the substrate.

12. The device according to claim 1, wherein the electrode, the source region and the drain region define a field effect transistor devoid of a gate electrode layer disposed on the semiconductor substrate.

13. A device for detecting biomolecules using a field effect transistor, the device comprising:
    a semiconductor substrate;
    a source region and a drain region of the field effect transistor separately provided on the substrate;
    a chamber formed at the substrate including a region between the source region and the drain region, the chamber configured to contain a sample including the biomolecules and an adsorptive medium on which the biomolecules are non-covalently adsorbed; and
    an electrode which applies a voltage to the sample in the chamber,
    wherein the electrode is disposed outside of the chamber, and
    wherein the biomolecules being detected are mobile with respect to the region between the source region and the drain region.

14. The device according to claim 13, wherein a channel is formed in the region between the source region and the drain region when the voltage is applied to the electrode, and the biomolecules in the sample are detected by measuring an electric signal between the source region and the drain region.

15. The device according to claim 13, wherein the field effect transistor is devoid of a gate electrode layer disposed on the semiconductor substrate.

* * * * *